United States Patent [19]

Dwyer

[11] 4,100,214

[45] Jul. 11, 1978

[54] ISOMERIZATION OF MONOCYCLIC ALKYL AROMATIC HYDROCARBONS

[75] Inventor: Francis G. Dwyer, West Chester, Pa.

[73] Assignee: Mobil Oil Corporation, New York, N.Y.

[21] Appl. No.: 684,512

[22] Filed: May 7, 1976

[51] Int. Cl.² ............................................. C07C 5/24
[52] U.S. Cl. ............................ 260/668 A; 260/668 R; 423/328
[58] Field of Search .................... 260/668 A; 423/328

[56] References Cited

U.S. PATENT DOCUMENTS

| 3,377,400 | 4/1968 | Wise | 260/668 A |
|---|---|---|---|
| 3,390,199 | 6/1968 | Burnett | 260/668 A |
| 3,702,886 | 11/1972 | Argauer et al. | 423/328 |
| 3,709,979 | 1/1973 | Chu | 423/328 |
| 3,832,449 | 8/1974 | Rosinski et al. | 423/328 |
| 3,907,914 | 9/1975 | Willis et al. | 260/668 A |

Primary Examiner—Veronica O'Keefe
Attorney, Agent, or Firm—Charles A. Huggett; Raymond W. Barclay; Dennis P. Santini

[57] ABSTRACT

A process is provided for isomerization of monocyclic alkyl aromatic hydrocarbons in a reaction zone maintained under conditions such that said isomerization is accomplished in the vapor phase.

10 Claims, No Drawings

ISOMERIZATION OF MONOCYCLIC ALKYL AROMATIC HYDROCARBONS

BACKGROUND OF THE INVENTION

1. Field of the Invention

The present invention relates to the use of specific diluents, i.e. toluene and $C_9+$ recycle material, with the monocyclic alkyl aromatic hydrocarbon feed in a vapor phase isomerization process over a catalyst comprising a crystalline aluminosilicate zeolite characterized by a silica/alumina mole ratio of at least 12 and a constraint index, hereinafter defined, within the approximate range of 1 to 12.

2. Description of the Prior Art

The catalytic rearrangement of alkyl groups present in alkyl aromatic hydrocarbons to provide one or more products suitable for use in the petroleum and chemical industries has heretofore been effected by a wide variety of catalysts. Acidic halides such as aluminum chloride, aluminum bromide, boron trifluoride —hydrogen fluoride mixtures, etc. have been used in the rearrangement of alkyl benzenes to provide valuable intermediates which find utility in the synthesis of rubber, plastic, fibers and dyes. Other catalysts which have been used include solid siliceous cracking-type catalysts such as silica-alumina and clays and platinum deposited on silica-alumina. Although various catalysts possess one or more desired characteristics, a majority of catalysts heretofore employed suffer from several disadvantages. Acidic halides such as aluminum chloride, for example, are partially soluble in the feed material and are easily lost from the catalyst zone. Catalysts of this type are also uneconomical because of their extreme corrosiveness and requirement for recovery from the effluent products. Other catalysts of the heterogeneous type, such as silica-alumina, platinum on alumina, etc., do not possess sufficient acidity to provide effective conversion and necessitate the use of relatively high temperatures above the order of 800° to 950° F. High temperatures frequently lead to coke formation which lowers the yield of desired product and necessitates frequent regeneration of the catalyst to remove coke. This results in reducing on-stream time and leads to high catalyst consumption due to loss of catalyst activity. Heterogeneous catalyst such as the crystalline aluminosilicates, both natural and synthetic, possess sufficient acidity but suffer the disadvantage or poor selectivity and aging as evidenced by "coke" make and the excessive amounts of disproportionated product formed in isomerization reactions.

SUMMARY OF THE INVENTION

This invention relates to the use of from about 3 to about 30 combined weight percent, preferably from about 5 to about 25 combined weight percent of toluene and $C_9+$ recycle material as diluents with the monocyclic alkyl aromatic hydrocarbon feed in vapor phase isomerization thereof. The isomerization reaction is carried out in the presence of a catalyst composition comprising a crystalline aluminosilicate zeolite characterized by a silica/alumina mole ratio of greater than 12 and a constraint index of from about 1 to about 12. The catalyst composition must contain, as replacement for at least a part of the original cations, cations of a metal of Group VIII of the Periodic Table of Elements, e.g. nickel, iron and/or cobalt. Further, it is preferred that the catalyst composition also contain, as replacement for at least a part of the original cations, hydrogen or hydrogen precursor cations.

The crystalline aluminosilicate zeolites used in the catalyst composition of the process of this invention are referred to generally as ZSM-5 type or as behaving like ZSM-5 and are represented by the general formulas, expressed in terms of mole ratios of oxides in the anhydrous state, as follows:

ZSM-5

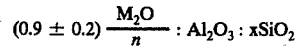
$$(0.9 \pm 0.2) \frac{M_2O}{n} : Al_2O_3 : xSiO_2$$

wherein M is a cation, predominately non-noble metal of Group VIII of the Periodic Table and/or hydrogen, n is the valence of M and X is at least 5,

ZSM-11

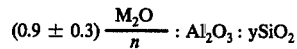
$$(0.9 \pm 0.3) \frac{M_2O}{n} : Al_2O_3 : ySiO_2$$

wherein M is a cation, predominately non-noble metal of Group VIII of the Periodic Table and/or hydrogen, n is the valence of M and y is from 20 to 90,

ZSM-12

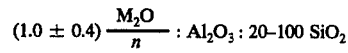
$$(1.0 \pm 0.4) \frac{M_2O}{n} : Al_2O_3 : 20\text{-}100\ SiO_2$$

wherein M is a cation, predominately non-noble metal of Group VIII of the Periodic Table and/or hydrogen and n is the valence of M, ZSM-35 and ZSM-38

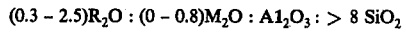
$$(0.3 - 2.5)R_2O : (0 - 0.8)M_2O : Al_2O_3 : > 8\ SiO_2$$

wherein R is an organic nitrogen-containing cation derived from ethylenediamine or pyrrolidine for ZSM-35 and from a 2-(hydroxyalkyl) trialkylammonium compound, wherein alkyl is methyl, ethyl or a combination thereof, for ZSM-38, and M is a cation, predominately non-noble metal of Group VIII of the Periodic Table and/or hydrogen.

DESCRIPTION OF SPECIFIC EMBODIMENTS

The catalyst composition useful in this invention comprises a crystalline aluminosilicate zeolite characterized by a silica/alumina mole ratio of at least 12 and a constraint index of from about 1 to about 12, non-limiting examples of which include ZSM-5, ZSM-11, ZSM-12, ZSM-35 and ZSM-38.

Zeolite ZSM-5 is taught by U.S. Pat. No. 3,702,886, issued November 14, 1972, the disclosure of which is incorporated herein by reference. In a preferred synthesized form, the zeolite ZSM-5 for use in the catalyst composition useful in this invention has a formula, in terms of mole ratios of oxides in anhydrous state, as follows:

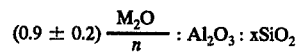
$$(0.9 \pm 0.2) \frac{M_2O}{n} : Al_2O_3 : xSiO_2$$

wherein M is selected from the group consisting of a mixture of alkali metal cations, especially sodium, and tetraalkylammonium cations, the alkyl groups of which preferably contain 2 to 5 carbon atoms, and x is at least 5. Particularly preferred is a zeolite having the formula in the anhydrous state as follows:

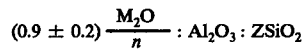
$$(0.9 \pm 0.2)\frac{M_2O}{n} : Al_2O_3 : ZSiO_2$$

wherein Z is from greater than 30 to about 350 or higher.

Zeolite ZSM-11 is taught by U.S. Pat. No. 3,709,979, issued January 9, 1973, the disclosure of which is incorporated herein by reference. In the as synthesized form, the zeolite ZSM-11 for use in the catalyst composition useful in this invention has a formula, in terms of mole ratios of oxides in the anhydrous state, as follows:

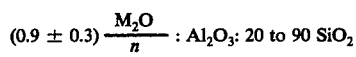
$$(0.9 \pm 0.3)\frac{M_2O}{n} : Al_2O_3 : 20 \text{ to } 90 \text{ SiO}_2$$

wherein M is a mixture of at least one of the quaternary cations of a Group V-A element of the Periodic Table and alkali metal cations, especially sodium. The original cations can be present so that the amount of quaternary metal cations is between 10 and 90 percent of the total amount of the original cations. Thus, the zeolite can be expressed by the following formula in terms of mole ratios of oxides:

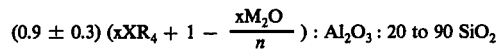
$$(0.9 \pm 0.3)(xXR_4 + 1 - \frac{xM_2O}{n}) : Al_2O_3 : 20 \text{ to } 90 \text{ SiO}_2$$

wherein R is an alkyl or aryl group having between 1 and 7 carbon atoms, M is an alkali metal cation, X is a group V-A element, especially a metal, and x is between 0.1 and 0.9.

Zeolite ZSM-12 is taught by U.S. Pat. No. 3,832,449, issued Aug. 27, 1974, the disclosure of which is incorporated herein by reference.

ZSM-35 is described in U.S. application Ser. No. 582,061, filed Nov. 29, 1974. This zeolite can be identified, in terms of mole ratios of oxides and in the anhydrous state, as follows:

$$(0.3 - 2.5)R_2O : (0 - 0.8)M_2O : Al_2O_3 : xSiO_2$$

wherein R is an organic nitrogen-containing cation derived from ethylenediamine or pyrrolidine, M is an alkali metal cation and x is greater than 8, and is characterized by a specified X-ray powder diffraction pattern.

In a preferred synthesized form, zeolite ZSM-35 has a formula, in terms of mole ratios of oxides and in the anhydrous state, as follows:

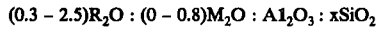
$$(0.4 - 2.5)R_2O : (0 - 0.6)M_2O : Al_2O_3 : ySiO_2$$

wherein R is an organic nitrogen-containing cation derived from ethylenediamine or pyrrolidine, M is an alkali metal, especially sodium, and y is from greater than 8 to about 50.

ZSM-38 is described in U.S. application Ser. No. 560,412, filed Mar. 20, 1975. This zeolite can be identified, in terms of mole ratios of oxides and in the anhydrous state, as follows:

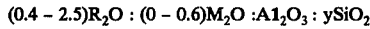
$$(0.3 - 2.5)R_2O : (0 - 0.8)M_2O : Al_2O_3 : xSiO_2$$

wherein R is an organic nitrogen-containing cation derived from a 2-(hydroxyalkyl) trialkylammonium compound, x is greater than 8 and M is an alkali metal cation, and is characterized by a specified X-ray powder diffraction pattern.

In a preferred synthesized form, the zeolite has a formula, in terms of mole ratios of oxides and in the anhydrous state, as follows:

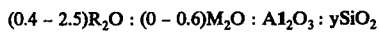
$$(0.4 - 2.5)R_2O : (0 - 0.6)M_2O : Al_2O_3 : ySiO_2$$

wherein R is an organic nitrogen-containing cation derived from a 2-(hydroxyalkyl) trialkylammonium compound, wherein alkyl is methyl, ethyl or a combination thereof, M is an alkali metal, especially sodium, and y is from greater than 8 to about 50.

The original cations of the above zeolites ZSM-5, ZSM-11, ZSM-12, ZSM-35 and ZSM-38 are replaced, in accordance with techniques well known in the art, at least in part, by ion exchange with hydrogen or hydrogen precursor cations and metal ions of Group VIII of the Periodic Table, e.g. nickel, iron and/or cobalt.

Although the zeolites herein described have unusually low alumina contents, i.e. high silica to alumina ratios, they are very active even when the silica to alumina ratio exceeds 30. The activity is surprising since catalytic activity is generally attributed to framework aluminum atoms and cations associated with these aluminum atoms. These catalysts retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. In many environments the zeolites of this class exhibit very low coke forming capability, conducive to very long times on stream between burning regenerations.

An important characteristic of the crystal structure of the zeolites for use herein is that they provide constrained access to, and egress from, the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type catalysts useful in this invention possess, in combination: a silica to alumina ratio of at least about 12; and a structure providing constrained access to the crystalline free space.

The silica to alumina ratio referred to may be deterdminded by conventional analysis. This ratio is meant to represent, as closely as possible, the ratio in the rigid anionic framework of the zeolite crystal and to exclude aluminum in the binder or in cationic or other form within the channels. Although catalysts with a silica to alumina ratio of at least 12 are useful, it is preferred to use catalysts having higher ratios of at least about 30. Such catalysts, after activation, acquire an intracrystalline sorption capacity for normal hexane which is greater than that for water, i.e. they exhibit "hydrophobic" properties. It is believed that this hydrophobic character is advantageous in the present invention.

The present invention provides a highly effective vapor phase isomerization process with a catalyst, the crystalline aluminosilicate zeolite portion of which, as suggested above, has a smaller pore size than those crystalline aluminosilicates previously used for such purpose. An example of this is zeolite ZSM-5 which has elliptical pores of approximately 4.8 × 7.1 Angstrom units.

The type zeolites useful in this invention freely sorb normal hexane and have a pore dimension greater than about 5 Angstroms, or, if elliptical in pore shape, at least the size of the pores in ZSM-5. In addition, the structure must provide constrained access to larger molecules. It is sometimes possible to judge from a known crystal structure whether such constrained access exists. For example, if the only pore windows in a crystal are formed by 8-membered rings of oxygen atoms, then access to molecules of larger cross-section than normal hexane is excluded and the zeolite is not of the desired type. Windows of 10-membered rings are preferred, although, in some instances, excessive puckering or pore blockage may render these catalysts ineffective. Twelve-membered rings do not generally appear to offer sufficient constraint to produce the advantageous conversions. Also, structures can be conceived due to pore blockage or other cause, that may be operative.

Rather than attempt to judge from crystal structure whether or not a catalyst possesses the necessary constrained access, a simple determination of the "constraint index" may be made by passing continuously a mixture of an equal weight of normal hexane and 3-methylpentane over a small sample, approximately 1 gram or less, of catalyst at atmospheric pressure according to the following procedure. A sample of the catalyst, in the form of pellets or extrudate, is crushed to a particle size about that of coarse sand and mounted in a glass tube. Prior to testing, the catalyst is treated with a stream of air at 1000° F for at least 15 minutes. The catalyst is then flushed with helium and the temperature adjusted between 550° and 950° F to give an overall conversion between 10% and 60%. The mixture of hydrocarbons is passed at 1 liquid hourly space velocity (i.e., 1 volume of liquid hydrocarbon per volume of catalyst per hour) over the catalyst with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10} (\text{fraction of n-hexane remaining})}{\log_{10} (\text{fraction of 3-methylpentane remaining})}$$

The constraint index approximates the ratio of the cracking rate constants for the two hydrocarbons. Catalysts suitable for the present invention are those having a constraint index in the approximate range of 1 to 12. Constraint Index (CI) values for some typical catalysts, including those useful herein, are:

| Crystalline Aluminosilicate | CI |
| --- | --- |
| ZSM-5 | 8.3 |
| ZSM-11 | 8.7 |
| ZSM-12 | 2 |
| ZSM-35 | 2 |
| ZSM-38 | 2 |
| Beta | 0.6 |
| ZSM-4 | 0.5 |
| H-Zeolon | 0.5 |
| REY | 0.4 |

| Crystalline Aluminosilicate | CI |
| --- | --- |
| Erionite | 38 |

It is to be realized that the above constraint index values typically characterize the specified zeolites but that such are the cumulative result of several variables used in determination and calculation thereof. Thus, for a given zeolite depending on the temperature employed within the aforenoted range of 550° F to 950° F, with accompanying conversion between 10% and 60%, the constraint index may vary within the indicated approximate range of 1 to 12. Likewise, other variables such as the crystal size of the zeolite, the presence of possibly occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination, with the probability, in some instances, of compounding variable extremes. However, in all instances, at a temperature within the above-specified range of 550° to 950° F, the constraint index will have a value for any given zeolite of interest herein within the approximate range of 1 to 12.

The specific zeolites described, when prepared in the presence of organic cations, are catalytically inactive, possibly because the intracrystalline free space is occupied by organic cations from the forming solution. They may be activated by heating, for example, in an inert atmosphere at 1000° F for one hour, followed by base exchange with ammonium salts and by calcination at 1000° F in air. The presence of organic cations in the forming solution may not be absolutely essential to the formation of this type zeolite; however, the presence of these cations does appear to favor the formation of this special type of zeolite. More generally, it is desirable to activate this type catalyst by base exchange with ammonium salts followed by calcination in air at about 1000° F for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite and clinoptilolite. The preferred crystalline aluminosilicates are ZSM-5, ZSM-11, ZSM-12, ZSM-35 and ZSM-38, with ZSM-5 particularly preferred.

In a preferred aspect of this invention, the catalysts hereof are selected as those having a crystal framework density, in the dry hydrogen form, of not substantially below about 1.6 grams per cubic centimeter. It has been found that zeolites which satisfy all three of these criteria are most desired for the present process. Therefore, the preferred catalysts of this invention are those having a constraint index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on page 19 of the article on Zeolite Structure by W. M. Meir. This paper, the entire contents of which are incorporated herein by reference, is included in "Proceedings of the Conference on Molecular Sieves, London, April 1967", published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolite is associated with its high crystal anionic framework density of not less than about 16 grams per cubic centimeter. This high density of course must be associated with a relatively small amount of free space within the crystal, which might be expected to result in more stable structures. This free space, however, is important as the locus of catalytic activity.

Crystal framework densities of some typical zeolites are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

Members of the above zeolites useful herein have an exceptionally high degree of thermal stability thereby rendering them particularly effective for use in processes involving elevated temperatures. In this connection, this group of zeolites appear to be some of the most stable zeolites known to date. However, it has been found that the process of this invention may be carried out at reactor bed temperatures not in excess of about 1100° F, which eliminates many undesirable reactions that may occur if carried out at higher temperatures. The deleterious effects of these reactions cause several basic problems for isomerization processes. At reactor bed temperatures substantially above 1100° F, the reactants and the products undergo degradation resulting in the loss of desired products and reactants. Undesirable residues are formed from the degradation reactions. These degradation products may lead to the formation of coke-like deposits on the active surfaces of the catalyst. As a result, these deposits rapidly destroy the high activity of the catalyst and greatly shorten its effective life. Such undesirable effects are obviated under the conditions and with the catalyst employed in the present process.

Members of the above group of zeolites for use in the catalyst composition of the present invention possess definite distinguishing crystalline structures as evidenced by the above U.S. Patents incorporated herein by reference.

The synthetic ZSM-35 zeolite possesses a definite distinguishing crystalline structure whose X-ray diffraction pattern shows substantially the significant lines set forth in Table 1.

TABLE 1

| Interplanar Spacing | Relative Intensity |
|---|---|
| 9.6 ± 0.20 | Very Strong-Very, Very Strong |
| 7.10 ± 0.15 | Medium |
| 6.98 ± 0.14 | Medium |
| 6.64 ± 0.14 | Medium |
| 5.78 ± 0.12 | Weak |
| 5.68 ± 0.12 | Weak |
| 4.97 ± 0.10 | Weak |
| 4.58 ± 0.09 | Weak |
| 3.99 ± 0.08 | Strong |
| 3.94 ± 0.08 | Medium-Strong |
| 3.85 ± 0.08 | Medium |
| 3.78 ± 0.08 | Strong |
| 3.74 ± 0.08 | Weak |
| 3.66 ± 0.07 | Medium |
| 3.54 ± 0.07 | Very Strong |
| 3.48 ± 0.07 | Very Strong |
| 3.39 ± 0.07 | Weak |
| 3.32 ± 0.07 | Weak-Medium |
| 3.14 ± 0.06 | Weak-Medium |
| 2.90 ± 0.06 | Weak |
| 2.85 ± 0.06 | Weak |
| 2.71 ± 0.05 | Weak |
| 2.65 ± 0.05 | Weak |
| 2.62 ± 0.05 | Weak |
| 2.58 ± 0.05 | Weak |
| 2.54 ± 0.05 | Weak |
| 2.48 ± 0.05 | Weak |

The synthetic ZSM-38 zeolite possesses a definite distinguishing crystalline structure whose X-ray diffraction patterns shows substantially the significant lines set forth in Table 1A.

TABLE 1A

| Interplanar Spacing | Relative Intensity |
|---|---|
| 9.8 ± 0.20 | Strong |
| 9.1 ± 0.19 | Medium |
| 8.0 ± 0.16 | Weak |
| 7.1 ± 0.14 | Medium |
| 6.7 ± 0.14 | Medium |
| 6.0 ± 0.12 | Weak |
| 4.37 ± 0.09 | Weak |
| 4.23 ± 0.09 | Weak |
| 4.01 ± 0.08 | Very Strong |
| 3.81 ± 0.08 | Very Strong |
| 3.69 ± 0.07 | Medium |
| 3.57 ± 0.07 | Very Strong |
| 3.51 ± 0.07 | Very Strong |
| 3.34 ± 0.07 | Medium |
| 3.17 ± 0.06 | Strong |
| 3.08 ± 0.06 | Medium |
| 3.00 ± 0.06 | Weak |
| 2.92 ± 0.06 | Medium |
| 2.73 ± 0.06 | Weak |
| 2.66 ± 0.05 | Weak |
| 2.60 ± 0.05 | Weak |
| 2.49 ± 0.05 | Weak |

These values were determined by standard technique. The radiation was the K-alpha doublet of copper, and a scintillation counter spectrometer with a strip chart pen recorder was used. The peak heights, I, and the positions as a function of 2 times theta, where theta is the Bragg angle, were read from the spectrometer chart. From these, the relative intensities, $100 \, I/I_o$, where $I_o$ is the intensity of the strongest line or peak, and k (obs.), the interplanar spacing in Angstrom units, corresponding to the recorded lines, were calculated. It should be understood that these X-ray diffraction patterns are characteristic of all the species of the above respectively identified zeolites. Ion exchange of the sodium ion with cations reveals substantially the same pattern with some minor shifts in interplanar spacing and variation in relative intensity. Other minor variations can occur depending on the silicon to aluminum ratio of the particular sample, as well as if it has been subjected to thermal treatment.

Zeolites ZSM-5, ZSM-11 and ZSM-12 for use in the process of this invention are prepared as indicated in their respective patents, incorporated herein by reference above.

Zeolite ZSM-35 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

TABLE 2

| $R^+$ | Broad | Preferred |
|---|---|---|
| $R^+ + M^+$ | 0.02 – 1.0 | 0.3 – 0.9 |
| $OH^-/SiO_2$ | 0.05 – 0.5 | 0.07 – 0.49 |
| $H_2O/OH^-$ | 41 – 500 | 100 – 250 |
| $SiO_2/Al_2O_3$ | 8.8 – 200 | 12 – 60 | wherein R is an organic nitrogen-containing cation derived from pyrrolidine or ethylenediamine and M is an alkali metal ion, and maintaining the mixture until crystals of the zeolite are formed. (The quantity of $OH^-$ is calculated only from the inorganic sources of alkali without any organic base contribution). Thereafter, the crystals are separated from the liquid and recovered. Typical reaction conditions consist of heating the foregoing reaction mixture to a temperature of from about 90° to about 400° F for a period of time of from about 6 hours to about 100 days. A more preferred temperature range is from about 150° to about 400° F with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is dried, e.g. at 230° F, for from about 8 to 24 hours.

Zeolite ZSM-38 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

TABLE 3

| $R^+$ | Broad | Preferred |
|---|---|---|
| $R^+ + M^+$ | 0.2 – 1.0 | 0.3 – 0.9 |
| $OH^-/SiO_2$ | 0.05 – 0.5 | 0.07 – 0.49 |
| $H_2O/OH^-$ | 41 – 500 | 100 – 250 |
| $SiO_2/Al_2O_3$ | 8.8 – 200 | 12 – 60 | wherein R is an organic nitrogen-containing cation derived from a 2-(hydroxyalkyl) trialkylammonium compound and M is an alkali metal ion, and maintaining the mixture until crystals of the zeolite are formed. (The quantity of $OH^-$ is calculated only from the inorganic sources of alkali without any organic base contribution). Thereafter, the crystals are separated from the liquid and recovered. Typical reaction conditions consist of heating the foregoing reaction mixture to a temperature of from about 90° to about 400° F for a period of time of from about 6 hours to about 100 days. A more preferred temperature range is from about 150° to about 400° F with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is thereafter dried, e.g. at 230° F for from about 8 to 24 hours.

For the isomerization process of this invention the suitable zeolite catalyst is employed in combination with a support or binder material such as, for example, a porous inorganic oxide support or a clay binder. Non-limiting examples of such binder materials include alumina, zirconia, silica, magnesia, thoria, titania, boria and combinations thereof, generally in the form of dried inorganic oxide gels and gelatinous precipitates. Suitable clay materials include, by way of example, bentonite and kieselguhr. The relative proportion of suitable crystalline aluminosilicate zeolite of the total composition of catalyst and binder or support may vary widely with the zeolite content ranging from between about 30 to about 90 percent by weight and more usually in the range of about 50 to about 80 percent by weight of the composition.

Operating conditions employed in the process of the present invention are critical. Such conditions as temperature, pressure, space velocity, molar ratio of the reactants, hydrogen to hydrocarbon mole ratio, and the presence of the diluents will have impportant affects on the process.

The process of this invention is conducted such that isomerization of the monocyclic alkyl aromatic hydrocarbon is carried out in the vapor-phase by contact in a reaction zone, such as, for example, a fixed bed of catalyst composition, under isomerization effective conditions, said catalyst composition being characterized, as synthesized, as comprising the above-defined zeolite which has been hydrogen or hydrogen precusor and Group VIII metal exchanged. This process may be conducted in either batch or fluid bed operation with attendent benefits of either operation readily obtainable.

The present isomerization process may be carried out at a temperature between about 450° and 900° F and at pressures ranging from about 50 psig up to about 500 psig. The weight hourly space velocities (WHSV) may be maintained at from about 0.1 to about 200, and the hydrogen/hydrocarbon mole ratio should be maintained at between about 0.1 and about 100. Within these limits the conditions of temperature and pressure will vary considerably depending upon equilibrium considerations and type of feed material. Optimum conditions are those in which maximum yields of desired isomer products are obtained and hence considerations of temperature and pressure will vary within a range of conversion levels designed to provide the highest selectivity and maximum yield.

The staring feed materials for isomerization to be employed in the process of the invention are preferably single ring aromatic hydrocarbons containing a minimum of two and a maximum of four alkyl group substituents on the ring. These feed materials may be illustrated by the following structural formula:

wherein R is a lower alkyl group, straight or branch chained, having 1 to about 4 carbon atoms and $n$ is an integer of 2 to 4. Thus, it is to be understood that the ring may contain from 2 to 4 alkyl substituents. Lower alkyl groups for R include especially methyl, ethyl, n-propyl, n-butyl, isopropyl or isobutyl or any combination thereof.

Specific compounds falling within the above structural formula include para-Xylene, meta-Xylene, ortho-Xylene, mesitylene (1, 3, 5-trimethylbenzene), durene (1, 2, 4, 5-tetramethylbenzene), hemimellitene (1, 2, 3-trimethylbenzene), pseudocumene (1, 2, 4-trimethylbenzene), prehnitene (1, 2, 3, 4-tetramethylbenzene), isodurene (1, 2, 3, 5-tetramethylbenzene), and 1, 3, 5-triethylbenzene.

Of the above listing of specific feed materials which may be used, the xylene isomers and pseudocumene are especially preferred.

The diluent material employed in the present process is comprised of both toluene and $C_9+$ recycle. The use of such diluent reduces xylene losses. The $C_9+$ recycle material is primarily composed of trimethylbenzenes, dimethylethylbenzenes and diethylbenzenes, which tend to increase xylene yields because the trimethylbenzenes shift the xylene disproportion equilibrium toward xylenes; the trimethylbenzenes compete with xylenes in the transalkylation reaction with ethylbenzene thus reducing the amount of xylenes going into $C_{10}$ product; and the dimethylethylbenzenes are deethylated over the present catalyst material producing xylenes as a product.

The amount of diluent is not narrowly critical and will vary within the range of 3 to 30 weight percent based on the feed material undergoing isomerization. Preferably, the amount of diluent is within the range of 5 to 25 weight percent.

The following specific examples will serve to illustrate the process of the present invention, without unduly limiting same.

EXAMPLE 1

A sodium silicate solution was prepared by mixing 8440 lb of sodium silicate (Q-Brand, Philadelphia Quartz Co.) and 586 gallons of water. After addition of 24 lbs Daxad 27 (W. R. Grace Chemical Division) the solution was cooled to approximately 55° F. An acid alum solution was prepared by dissolving 293 lb aluminum sulfate (17.2% $Al_2O_3$), 733 lb sulfuric acid (93%) and 377 lb sodium chloride in 602 gallons of water. The solutions were passed through a mixing nozzle and into a stirred autoclave. During the mixing operation, 1200 lb of sodium chloride was added to the vessel. The resulting gel was thoroughly agitated and heated to 200° F in the closed vessel. After reducing agitation, an organic solution prepared by mixing 568 lb tri-n-propylamine, 488 lb n-propylbromide was reacted for 14 hours at a temperature of 200°–220° F. At the end of this period, agitation was increased and these conditions maintained until the ZSM-5 crystallinity reached at least 65%. Temperature was then increased to 320° F until crystallization was complete. The residual organics were flashed from the autoclave and the product slurry was cooled.

The product was washed by decantation using Rohm and Haas Permafloc C-7 flocculant. The washed product containing less than 1% sodium was filtered and dried. The weight of dried zeolite was approximately 2300 lb. It was determined to be zeolite ZSM-5 having a silica/alumina ratio of greater than 12, a constraint index of about 8.3 and a crystal framework density of about 1.79.

The dried product was mixed with Continental Oil Catapal SB (α alumina monohydrate) and water (65% zeolite, 35% alumina binder on ignited bases) then extruded to form of 1/16 inch pellet.

An 1120 gram quantity of dried extrudate was calcined at 1000° F for 3 hours in the presence of $N_2$ gas flow at a rate of 3 volumes of $N_2$ per volume of extrudate per minute. The temperature was brought up at a heating rate of about 3°–5° F per minute. The precalcined extrudate was ammonium exchanged with 1N $NH_4NO_3$ solution, 5 ml of solution for every gram extrudate. After two 1 hour exchanges at room temperature, the extrudate was drained, washed and dried. The final Na content of the extrudate was found to be 0.03 wt. percent.

The ammonium exchanged product was calcined in air at 1000° F for three hours. The air flow rate was 3 volumes per volume of extrudate per minute. The heating rate was 3°–5° F per minute.

A 100 gram quantity of the ammonium exchanged extrudate was then Ni exchanged with 1.0N $Ni(NO_3)_2$ solution (5 ml to every gram extrudate) at 190° F for 4 hours. After exchange, the extrudate was drained, washed Ni free and dried. The Ni exchanged product was calcined in air at 1000° F for three hours. The air flow rate was 3 volumes per volume of extrudate per minute. The heating rate was 3°–5° F per minute. The final product was analyzed to have 1.0 wt. percent Ni and 0.02 wt. percent Na.

EXAMPLES 2–5

The catalyst material prepared in Example 1 is placed in a reactor and contacted with a mixed xylene feed (see Table 4, hereinafter presented) containing additionally 5 combined weight percent diluent composed of toluene and $C_9+$ recycle material (Primarily trimethylbenzenes, dimethylethylbenzenes and diethylbenzenes) under vapor-phase isomerization reaction conditions identified in Table 4. The liquid product analysis as well as normalized ortho-, meta-, and para-xylene content of the product are also listed in Table 4.

TABLE 4

| Example No. | | 2 | 3 | 4 | 5 |
|---|---|---|---|---|---|
| Operating Conditions | | | | | |
| Temperature, ° F | | 602 | 601 | 601 | 596 |
| Pressure, psig | | 203 | 206 | 206 | 205 |
| $H_2$/HC, mole ratio | | 1 | 1 | 1 | 1 |
| WHSV | | 10 | 20.1 | 39.6 | 80.7 |
| Time on stream, hr. | | 2 | 3 | 3.5 | 4 |
| Liquid Product Analysis, wt. % | | | | | |
| | Feed | | | | |
| Benzene | 0.06 | 2.3 | 1.3 | 0.8 | 0.4 |
| Ethylbenzene | 19.8 | 14.9 | 16.9 | 18.1 | 19.1 |
| p-Xylene | 2.7 | 18.1 | 18.2 | 17.7 | 15.6 |
| m-Xylene | 49.4 | 39.7 | 39.9 | 40.1 | 41.0 |
| o-Xylene | 23.1 | 16.2 | 16.6 | 17.4 | 19.1 |
| Diluent | 5.0 | ~5.0 | ~5.0 | ~5.0 | ~5.0 |

TABLE 4-continued

| Example No. | 2 | 3 | 4 | 5 |
|---|---|---|---|---|
| (Toluene+$C_9^+$Recycle) Xylene Loss, wt. % | 1.3 | 0.5 | 0.1 | (0.5) |
| Ethylbenzene Conversion, wt. % | 24.9 | 15.1 | 8.8 | 3.9 |
| Normalized | | | | |
| p-Xylene | 24.4 | 24.3 | 23.6 | 20.6 |
| m-Xylene | 53.7 | 53.5 | 53.3 | 54.2 |
| o-Xylene | 21.9 | 22.2 | 23.1 | 25.2 |

What is claimed is:

1. A process for effecting catalytic isomerization of xylenes which comprises contacting said xylenes in the vapor phase with hydrogen at a temperature of from about 450° to about 900° F, a pressure of from about 50 psig to about 500 psig, a hydrogen/hydrocarbon mole ratio of from about 0.1 to about 100 and a weight hourly space velocity of from about 0.1 to about 200 in the presence of from about 3 to about 30 combined weight percent, based upon weight of the xylene feed, of diluent of toluene and $C_9^+$ recycle material and a crystalline aluminosilicate zeolite characterized by a silica/alumina mole ratio of greater than 12 and a constraint index within the approximate range of 1 to 12 and containing cations which are selected from the group consisting of iron, nickel and cobalt.

2. The process of claim 1 wherein said zeolite is ZSM-5, ZSM-11, ZSM-12, ZSM-35 or ZSM-38.

3. The process of claim 2 wherein said zeolite is ZSM-5.

4. The process of claim 1 wherein said zeolite is combined in an amount of from about 30 to about 90 weight percent in a binder therefor.

5. The process of claim 4 wherein said binder is alumina.

6. The process of claim 2 wherein said zeolite is combined in an amount of from about 30 to about 90 weight percent in a binder therefor.

7. The process of claim 6 wherein said binder is alumina.

8. The process of claim 1 wherein said cations are nickel.

9. The process of claim 1 wherein said diluent is present at from about 5 to about 25 weight percent of the xylene mixture feed.

10. The process of claim 2 wherein said diluent is present at from about 5 to about 25 weight percent of the xylene mixture feed.

* * * * *

UNITED STATES PATENT AND TRADEMARK OFFICE
CERTIFICATE OF CORRECTION

PATENT NO. : 4,100,214
DATED : July 11, 1978
INVENTOR(S) : FRANCIS G. DWYER

It is certified that error appears in the above-identified patent and that said Letters Patent are hereby corrected as shown below:

Column 13, TABLE 4 - continued: In the line commencing with "Xylene Loss, wt. %", the "(0.5)" should be in the column headed by the number "5".

Signed and Sealed this

*Fifteenth* Day of *May 1979*

[SEAL]

Attest:

RUTH C. MASON
*Attesting Officer*

DONALD W. BANNER
*Commissioner of Patents and Trademarks*